US007375079B2

United States Patent
Gordon et al.

(10) Patent No.: US 7,375,079 B2
(45) Date of Patent: *May 20, 2008

(54) PREVINS AS SPECIFIC INHIBITORS AND THERAPEUTIC AGENTS FOR BOTULINUM TOXIN B AND TETANUS NEUROTOXINS

(75) Inventors: Richard K. Gordon, Potomac, MD (US); Deborah R. Moorad, Silver Spring, MD (US); Bhupendra P. Doctor, Potomac, MD (US); Gregory E. Garcia, Silver Spring, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/268,757

(22) Filed: Nov. 4, 2005

(65) Prior Publication Data

US 2006/0247176 A1   Nov. 2, 2006

Related U.S. Application Data

(63) Continuation of application No. 10/854,646, filed on May 27, 2004, now abandoned, which is a continuation of application No. 09/979,101, filed as application No. PCT/US00/13215 on May 15, 2000, now Pat. No. 7,235,521.

(60) Provisional application No. 60/134,446, filed on May 17, 1999.

(51) Int. Cl.
*A61K 38/00* (2006.01)

(52) U.S. Cl. ............... 514/2; 514/15; 530/300; 435/7.1; 435/320.1; 435/325; 424/239.1; 536/23.5

(58) Field of Classification Search ............ 514/15, 514/2; 435/7.1, 320.1, 325; 536/23.5; 424/239.1; 530/327, 300

See application file for complete search history.

(56) References Cited

U.S. PATENT DOCUMENTS 6,573,244 B1 * 6/2003 Gordon et al. ............... 514/15

FOREIGN PATENT DOCUMENTS

WO    WO 99/37664 A1    7/1999

OTHER PUBLICATIONS

Garcia et al., Botulinum B Toxin Activity is Inhibited by Burorin I:, FASEB J., 12, A-1492 (1998).
Boksa et al., "Characterization of substance P and somatostatin receptors on adrenal chromaffin cells using structural analongs", Brain Res., (1982), 245(2), pp. 275,283.
Park et al., "A Novel Antimicrobial Peptide from Bufo bufo gargarizans", Biochemical and Biophysical Research Communication, 218, pp. 408-413, (1996).
Norinder et al., "A quantitative structure-activity relationship study of some substance P-related peptides", K/ (e[tode Res. 49. pp. 155-162, (1997).
Niedzwiecki et al., "Substrate Specificity of the Human Matrix Metalloproteinase Stromelysin and the Development of Continuous Fluorometric Assays". Biochemistry 31, pp. 12618-12623, (1992).

* cited by examiner

*Primary Examiner*—Chih-Min Kam
(74) *Attorney, Agent, or Firm*—Elizabeth Arwine

(57) ABSTRACT

The compounds of the invention are generally described by the formula:

$$B_1Z^*_2B_3Z^*_4X^*_5Q_6F_7X_8X_9X_{10}X_{11}, \quad (1)$$

$$B_1X_2X_3X_4X_5Q_6F_7X_8X_9X_{10}X_{11}, \text{ or} \quad (2)$$

$$B_1Z_2B_3X_4Z_5Q_6F_7Z_8X_9X_{10}X_{11} \quad (3)$$

and the salts, esters, amides, and acyl forms thereof. Each position represented by a letter indicates a single amino acid residue: B is a basic of polar/large amino acid or a modified form thereof; X is a small or hydrophobic amino acid or a modified form thereof; X* is a small or polar/large amino acid or a modified form thereof; Z is a polar/large or hydrophobic amino acid or a modified form thereof; Z* is Proline or a polar/large of hydrophobic amino acid or a modified form thereof. As described below, one or more of the peptide linkages between the amino acid residues may be replaced by a peptide linkage mimic.

These compounds may be used as molecular building blocks to create compounds that are optimized for inhibiting the protease activity of Botulinum b and tetanus toxins.

10 Claims, 8 Drawing Sheets

| | |
|---|---|
| RPKPQQFFGLM (SEQ ID NO:1)<br>CCCCHHHHHH | Substance P |
| RAKPQQFFGLM (SEQ ID NO:5)<br>HHCHHHHHHH | change to promote helix structure in the upstream sequence. |
| RAKAQQFFGLM (SEQ ID NO:6)<br>HHHHHHHHHH | changes to promote helix structure |
| RAKAQQFPGLM (SEQ ID NO:7)<br>HHHHHHCHHH | Changes introduce a helix break following the QF site |
| RAKLQQFPGLM (SEQ ID NO:8)<br>HHHHHHCCHHH | Substitutions which result in more turn character following the QF site |
| RAKGLQFPGLM (SEQ ID NO:9)<br>HHHCCCCCCHH | Substitutions which result in more turn character following the QF site |
| RAGLGQFFGLM (SEQ ID NO:10)<br>HHHHCCHHHHH | Substitutions which result in less turn character around the QF site |
| DAARAKGLQFPGLMAKLK (SEQ ID NO:11)<br>HHHHHHCCCCHHHHHHHH | Mixture of substitutions and mutations which give extended helices upstream and downstream from the QF site which strengthens the interaction of the helices to each other and/or BttxB (GOR) |
| DAARAKGLQFPGLLAKLK (SEQ ID NO:12)<br>HHHHHHCCCEHHHHHHHH | Mixture of substitutions and mutations which give extended helices upstream and downstream from the QF site which strengthens the interaction of the helices to each other and/or BttxB and removes potential M oxidation problems (GOR) |
| TRSRAKGLQFPGLMVHRL (SEQ ID NO:13)<br>HHHHHCCCECHHHHHHHH | Alternative substitutions and mutations which give extended helices upstream and downstream from the QF site which strengthens the interaction of the helices to each other and/or BttxB |
| XQF--------------Y<br>(SEQ ID NO:14) | Replacement of downstream sequence with at least one carbon spacer and a hydrophobic amino acid to provide a potentiating amino acid downstream of the QF site |
| -- = Spacer<br>X = suitable core sequence (formula 1, 2, 3) upstream of QF<br>Predicted structures by Gibrat method or by GOR when indicated.<br>H = helix<br>C = coil, random, potential turn<br>E = sheet | |

Core structures within the scope of the invention.

Fig. 7

PREVINS AS SPECIFIC INHIBITORS AND THERAPEUTIC AGENTS FOR BOTULINUM TOXIN B AND TETANUS NEUROTOXINS

This application is a continuation of U.S. application Ser. No. 10/854,646, filed May 27, 2004, now abandoned, which is a continuation of U.S. application Ser. No. 09/979,101, filed Apr. 8, 2002, now U.S. Pat. No. 7,235,521, which is a 371 of PCT/US00/13215, filed May 15, 2000, which claims benefit of U.S. Provisional Application No. 60/134,446, filed May 17, 1999.

TECHNICAL FIELD

The invention relates to a class of peptide and peptide-like compounds, "Previns" which inhibit the enzymatic activity of Botulinum toxin B and Tetanus neurotoxins and may be used as molecular building blocks for creating compounds which are optimized for inhibiting the protease activity of Botulinum toxin B and Tetanus neurotoxins.

BACKGROUND OF THE INVENTION

The Botulinum toxins (Bttxs) are among the most potent toxins to animals, e.g. the $LD_{50}$ in mice is about 1 ng/kg. Bttxs comprise a family of seven distinct serotypes (A-G). Bttxs are composed of two subunits comprising a 100 kdal nerve-cell targeting heavy chain and a 50 kdal endoproteolytically active light chain. These toxins are Zn-metalloproteases and contain a Zn-protein binding motif HEXXH.

However, Zn-metalloprotease inhibitors, such as angiotensin converting enzyme inhibitors, captopril and phosphoramidon, are not effective inhibitors of Bttxs. Although Zn-chelators inhibit Bttx protease activity in vitro, they merely delay the protease activity in vivo and in tissue preparations comprising intact nerve and muscles cells and/or tissues. Furthermore, some Zn-chelators are toxic at concentrations necessary to delay the Bttx protease activity. Although dithiocarbamates inhibit other Zn-containing proteins such as SOD, they are ineffective against the Bttx serotype B (BttxB). Clearly, inhibitors of the various Bttx serotypes, such as BttxB, are needed.

BttxB specifically cleaves synaptobrevin (VAMP2) between glutamine 76 and phenylalanine 77 (QF bond or cleavage site). There is an obligatory requirement for a relatively long substrate for the in vivo target VAMP2 as shown by efforts to produce a minimum length substrate. It has been shown that 30 amino acids of VAMP2 are required and 40 amino acids of VAMP2 are required for optimum cleavage. See Shone, C. C. et al. (1993) Eur. J. Biochem. 217:965-971. V2, a peptide derived from VAMP2, is a sequence of 10 amino acids located 4 residues upstream from the cleavage site, and was found to inhibit Bttx activity. See Pellizzari R. et al. (1996) J. Biol. Chem. 271:20353-20358. In VAMP2, a mutation of the C-terminal amino acids had little effect; whereas a helix disrupting substitution of Pro for Ala inhibited BttxB activity by 28%. Further, replacement of several negatively charged amino acids led to almost complete inactivity. See Whitcome, M, et al. (1996) FEBS Let. 386:133-136).

Computer-aided secondary structure analysis of VAMP2 predicted two stretches of α-helical structure flanking the cleavage site QF. See Witcome, M. R. et al. (1996) FEBS Let. 386: 133-136. Computer-aided tertiary structure analysis indicates that the two helices could self associate to form a supersecondary structure of a helix bundle with the helices separated by a reverse turn. See Lebeda F. J., et al. (1996) Med. Defense Biosci. Rev. 204.

The above results indicate that more than just the QF bond is required to be recognized by the toxin for substrate cleavage.

We have previously described a new class of compounds, Buforinins, that have a characteristic conformation, a QF bond, and inhibit BttxB protease activity.

Recently, however, we have elucidated core structures present in these Buforinins and core structures exemplified by Substance P which may serve as the foundation structure or molecular building block of compounds which inhibit the protease, activity of BttxB and Tttx. These core sequences may be the elemental structure of compounds which inhibit the protease activity of BttxB and Tttx. These core sequences and their uses are disclosed herein below.

SUMMARY OF THE INVENTION

The invention is directed to the core structures called "Previns" which have an internal QF bond and the ability to inhibit BttxB protease activity. As the tetanus toxin cleavage site is the same as BttxB, the core structures may also serve as the core structures of compounds that competitively inhibit tetanus protease activity.

Thus, in one aspect, the invention is directed to compounds having a structure of the formula:

$$B_1Z^*_2B_3Z^*_4X^*_5Q_6F_7X_8X_9X_{10}X_{11} \qquad (1),$$

$$B_1X_2X_3X_4X_5Q_6F_7X_8X_9X_{10}X_{11} \qquad (2), \text{ or}$$

$$B_1X_2B_3X_4Z_5Q_6F_7Z_8X_9X_{10}X_{11} \qquad (3)$$

and the salts, esters, amides, and acyl forms thereof. Each position represented by a letter indicates a single amino acid residue: B is a basic or polar/large amino acid or a modified form thereof; X is a small or hydrophobic amino acid or a modified form thereof; X* is a small or polar/large amino acid or a modified form thereof; Z is a polar/large or hydrophobic amino acid or a modified form thereof; Z* is Proline or a polar/large or hydrophobic amino acid or a modified form thereof. As described below, one or more of the peptide linkages between the amino acid residues may be replaced by a peptide linkage mimic.

In other aspects, the invention is directed to recombinant materials useful for the production of those peptides of the invention that contain gene-encoded amino acids, as well as plants or animals modified to contain expression systems for the production of these peptides. The invention also includes methods to prepare and manipulate these recombinant materials.

In addition, the invention is directed to pharmaceutical compositions containing compounds, containing the core structure of the invention, as active ingredients and to compositions which contain expression systems for the production of the peptides. The invention is also directed to methods to prepare compounds containing the core structure of the invention synthetically, to antibodies specific for these compounds, and to the use of the compounds as preservatives, therapeutics, and prophylactics.

The invention is also directed to the use of the compounds containing the core structures of the invention in assays for detection of BttxB and Tttx by the use of selective inhibition and for determining inhibitors and substrates for a given toxin.

The present invention relates to materials, compositions, kits and methods for inhibiting the enzymatic activity of Botulinum toxin B and Tetanus neurotoxins. The invention further relates to materials, compositions, kits and methods for preventing or treating toxic poisoning such as Botulinum toxin B and tetanus poisoning. The kits can provide single or multiple dosage and can include other conventional ancillary materials such as instructions, solutions and compositions needed for operation. The compositions and solutions may be placed in containers, test tubes, etc. Containers could be similar to those employed in insect/snake bite kits that includes an injector which provides compounds containing the core structure of the invention and TCEP in separate chambers. A kit for determining whether a sample contains a compound having the core structure of the invention, the amount of said compound or the type of said compound may include antibodies immunospecific for the core structure.

A kit for determining whether a sample contains a Botulinum toxin or the type of the Botulinum toxin may include antibodies immunospecific for at least one compound containing the core structure having an interaction with a Botulinum toxin. Likewise, a kit for determining whether a sample contains a Tetanus toxin would include antibodies immunospecific for at least one compound containing the core structure of the invention having an interaction with a Tetanus toxin.

Another embodiment includes Buforin I along with one or more known peptide inhibitors associated with the decontamination of Botulinum B and/or Tetanus toxins. Additionally, the kits may also include a stable peptide mixture or powder which includes compounds having the core structures of the invention for sprinkling over food or wounds for detoxification.

Yet another embodiment includes the use of the compounds of the invention as molecular building blocks to construct compounds optimized for inhibition of the protease activity of BttxB and Tttx.

DESCRIPTION OF THE DRAWINGS

FIG. 7 shows typical compounds of the formula (1), (2) or (3).

DETAILED DESCRIPTION OF THE INVENTION

Figure 1:
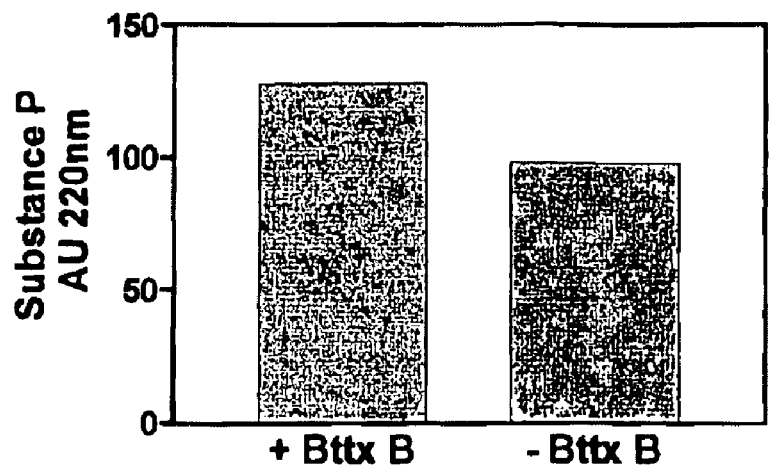
FIG. 1 shows that although Substance P is not a substrate of BttxB, it is an inhibitor.

In our search for BttxB inhibitors, we investigated peptides that contain the QF cleavage site but are not identical in primary sequence to VAMP2 surrounding the QF site. Substance P, an 11 amino acid peptide containing the QF bond is not a substrate of BttxB. See Example 1 and 2; and FIG. 1. This result supports the preferred helix-turn-helix and/or long substrate hypothesis.

Figure 2:
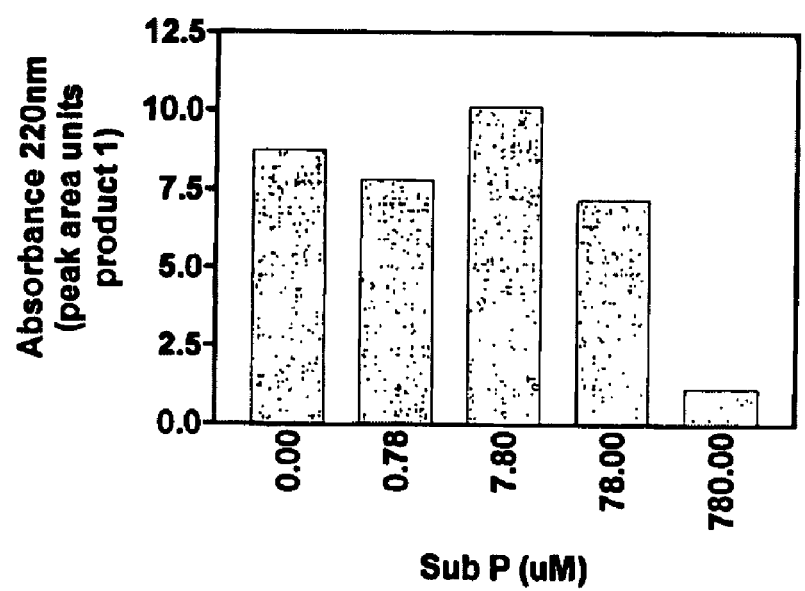
FIG. 2 shows the degree of BttxB inhibition of Substance P.
Figure 3:
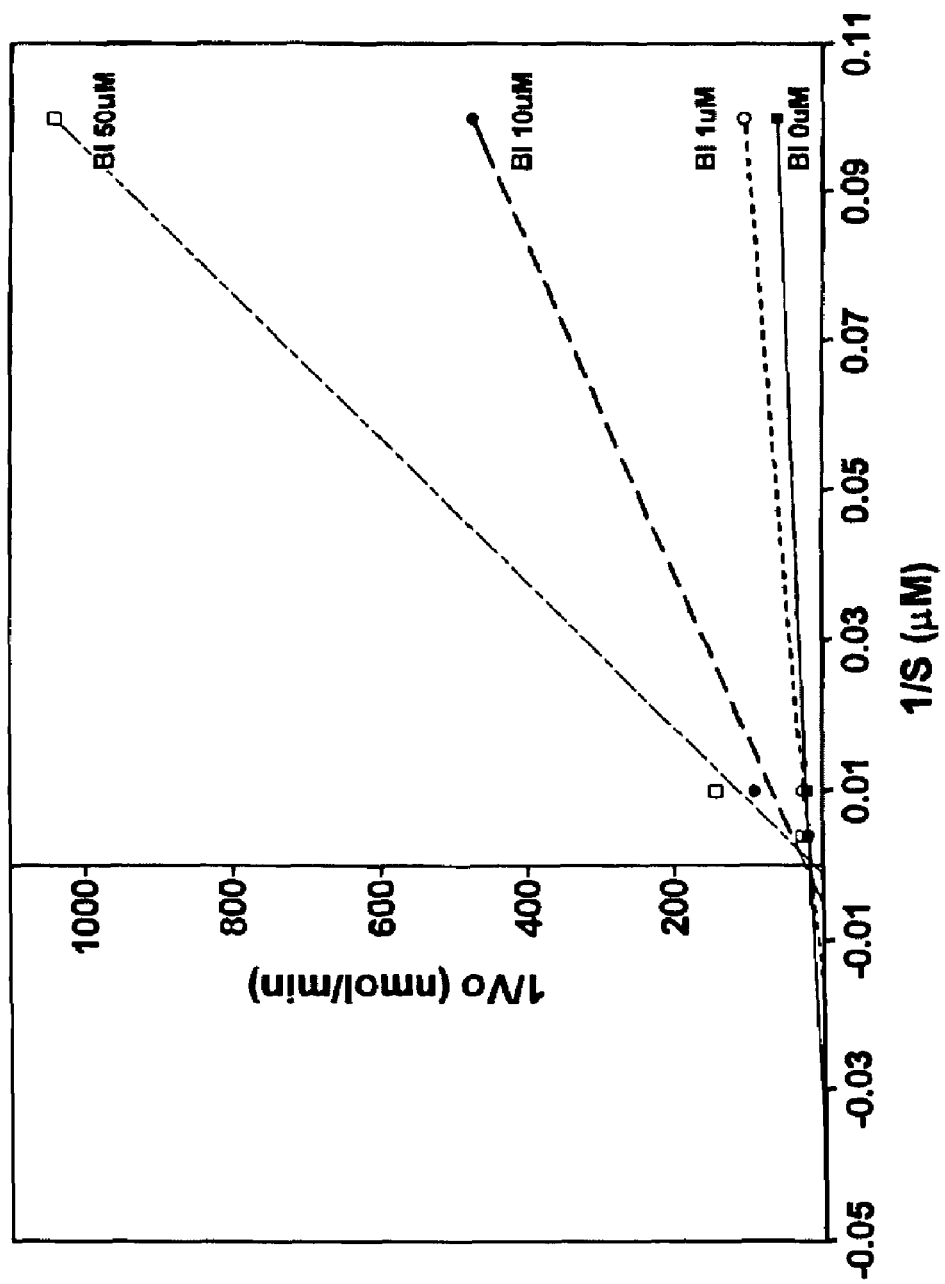
FIG. 3 shows a double reciprocal plot of inhibition of BttxB endoprotease activity by Buforin I.
Figure 4:
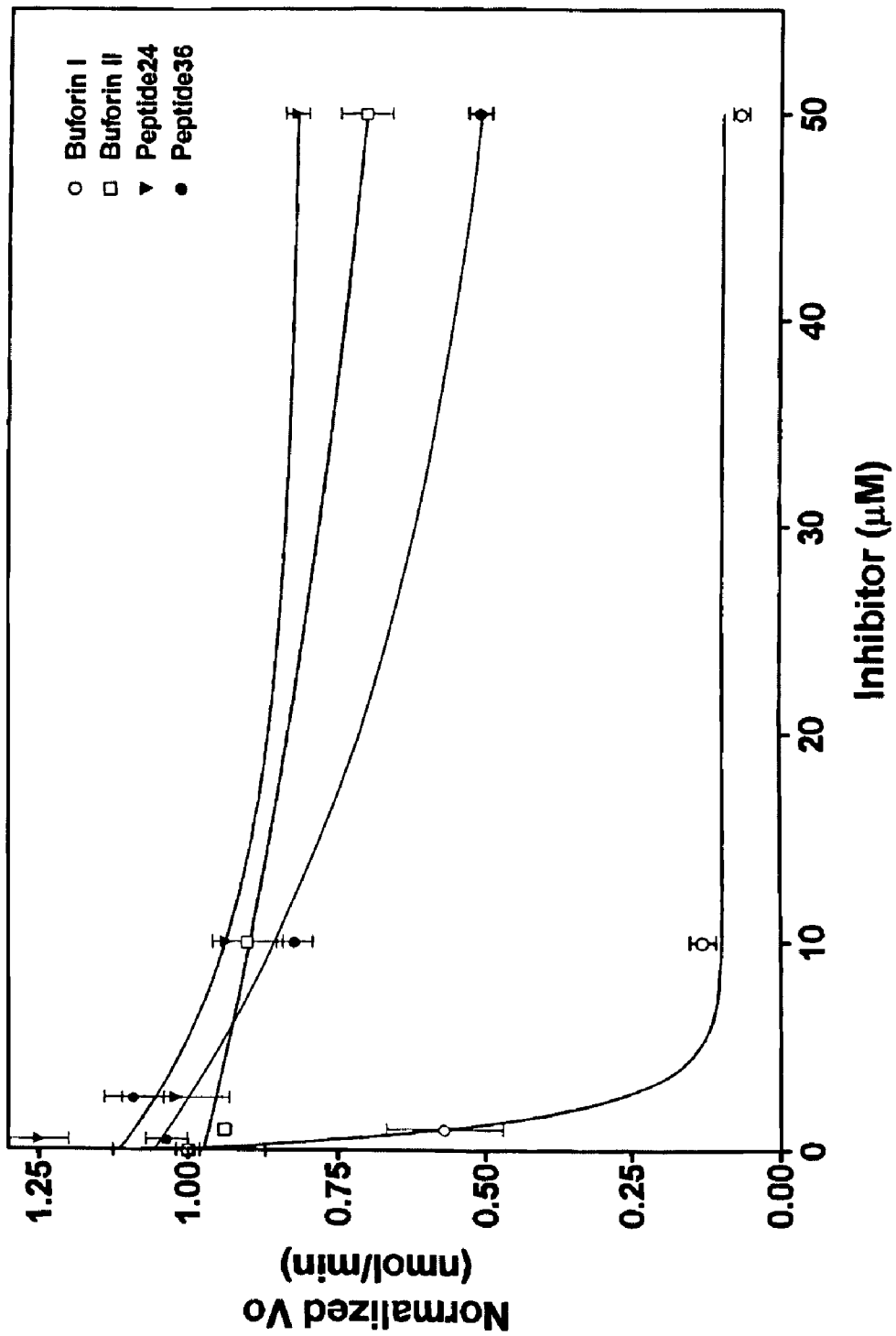
FIG. 4 illustrates the inhibition of BttxB endoprotease activity by various Buforinins.

Buforin I (B-I) is a peptide isolated from the stomach of the Asian toad *Bufo bufo gargarizans* which has a QF bond. Therefore, we used our endopeptidase assay to determine if B-I is a substrate or an inhibitor of BttxB protease activity. We found that B-I is not a substrate for BttxB and that B-I dose-dependently and competitively inhibits BttxB activity. See FIGS. 2 and 3. The extent of inhibition gave an $IC_{50}=1\times10^{-6}$ M. See FIG. 4. This was a surprising result as B-I is only 18% homologous for conserved amino acids with VAMP2 55-94. See Table 1.

TABLE I

Sequence alignment of VAMP2, Buforin I and Buforin I derivative peptides and Substance P

| Peptide | Sequence |
| --- | --- |
| $VAMP2_{55-94}$ | ERDQKLSELDDRADALQAGASQFET-SAAKLKRKYWWKNLK (SEQ ID NO: 16) |
| Buforin I[a] | AGRGKQGGKVRAKAKTRSSRAGLQFPVGRVHRLLRKGNY (SEQ ID NO: 17) |
| Buforin II[b] | TRSSRAGLQFPVGRVHRLLRK (SEQ ID NO: 2) |
| Peptide24[c] | TRSSRAGLQFPVGRVHRLLRKGNY (SEQ ID NO: 18) |
| Peptide36[c] | AGRGKQGGKVRAKAKTRSSRAGLQFPVGRVHRLLRK (SEQ ID NO: 19) |
| Sub P[d] | RPKPQQFFGLM (SEQ ID NO: 5) |

[a]Archer, B. T. III., et al. (1990) J. Biol. Chem. 265: 17267-17273.
[b]Park C. B., et al. (1996).
[c]Garcia, G. E. et al. (1998).
[d]Chang, M. M. et al. (1971) Nat. New Biol. 232: 86-87.

We then evaluated truncated B-I peptides with our endopeptidase activity assay. The truncated peptides we evaluated are Peptide 36 which contains amino acids 1-36 of B-I and Peptide 24 which contains amino acids 16-39 of B-I. Like B-I, these truncated peptides were not substrates of BttxB; however, the truncated peptides are less effective inhibitors of BttxB activity as B-I. See FIG. 2. Peptide 36 was about 50% as effective as B-I. Peptide 24 was about 25% as effective as B-I. We also evaluated Buforin II (B-II), which contains amino acids 16-36 of B-I, and found that B-II was 25% as effective as B-I.

Figure 5:
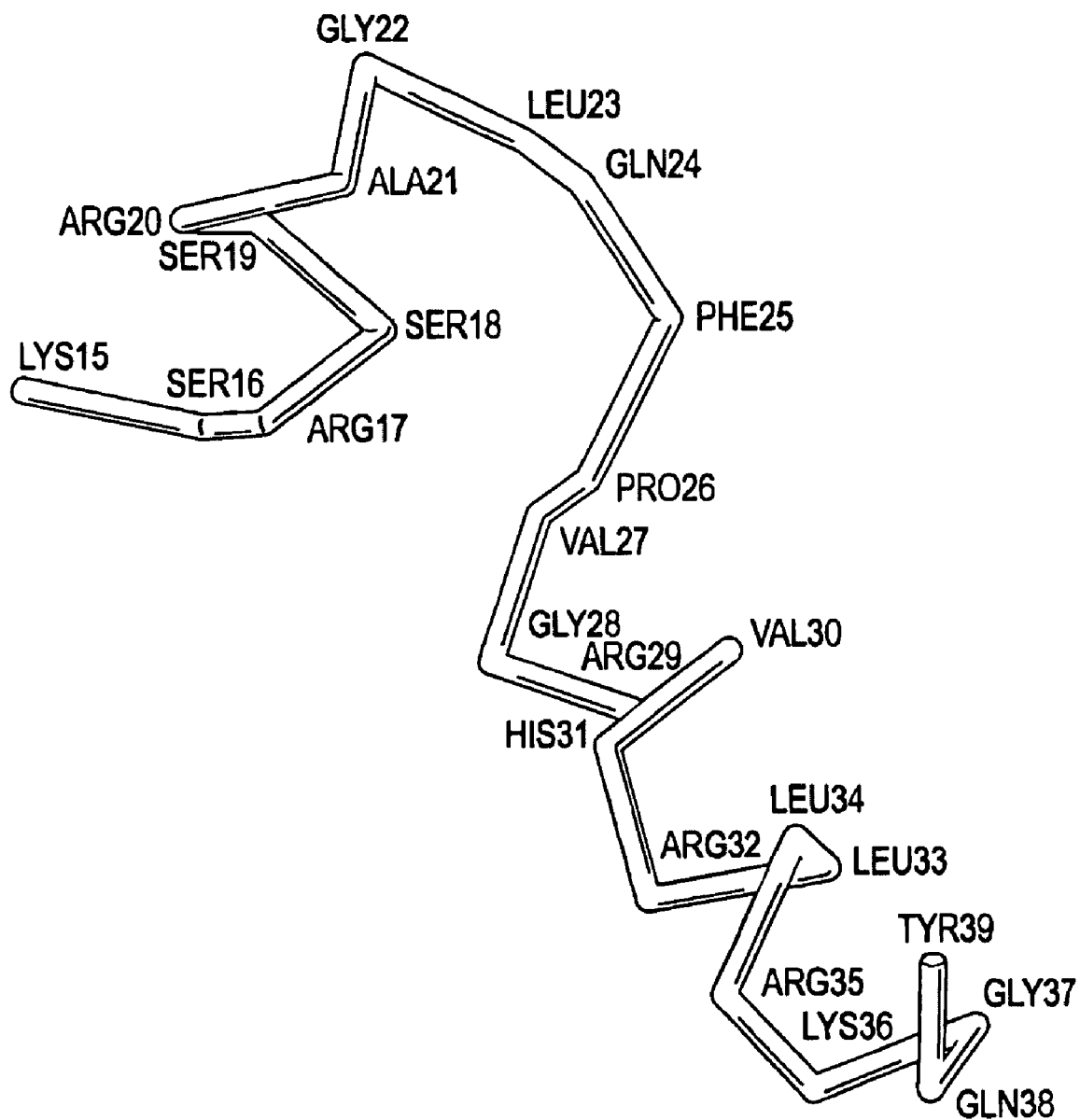
FIG. 5 illustrates the X-ray crystallographic structure of avian chromosomal protein histone octamer H2A residues Lys15-Try39 produced by Brookhaven Protein Database #1 HIO.

B-I is derived from histone protein 2A (H2A) of the toad which is nearly identical to the sequence of avian H2A. See Table 2A and see Park, C. B., et al. (1996) Biochem. Biophys. Res. Comm. 218:408-413. Table 2B shows the comparison of relevant amino acid sequences between Substance P and Buforin II. X-ray crystallographic analysis of the chicken histone protein particle shows that, for the region K15 to Y39, there are helices upstream and downstream of the QF site. See FIG. 5 and See Arents, G., et al. (1991) PNAS 88:10148-52 and Wang, S. W., et al. (1985) Nucleic Acids Res. 13:1369-138. Also, NMR analysis of B-II shows that the region upstream from the QF site could form α-helix. See Yi, et al. (1996) FEBS Lett. 398:87-90.

TABLE 2A

H2A comparison of chicken to toad for relevant amino acid sequences

| Source | Database[GB] Accession no. | | % Homology[a] |
|---|---|---|---|
| *Bufo bufo gagarizans* | BBU70133 | GRGKQGGKVRAKAKTRSSRAGLQFPVGRVHRLLRKGNY (SEQ ID NO: 20) | |
| *Gallus gallus* | X02218 | GRGKQGGKARAKAKSRSSRAGLQFPVGRVHRLLRKGNY (SEQ ID NO: 21) | 100 |

The suffix [GB] signifies accession numbers in the GenBank database.
[a]Homology to toad sequence. Similarity; basic: Arg, Lys; acidic: Asp, Glu; polar: Asn, Gln; hydrophobic: Ala, Ile, Leu, Met, Val; aromatic: Phe, Tyr, Trp; Hze. Ala, Ser, Thr.
[1] Kim, H. S., Park, C. B., Kim, M. S., Kim, S. C. (96) biochem. Biophys. Res. Comm. 229: 381-387.
[2] Wang, S. W., Robins, A. J., d = Andrea, R Wells, J. R. (85) Nucleic Acids Res. 13: 1369-1387.

TABLE 2B

Comparison of the relevant amino acid sequences between Substance P and Buforin II

| Source | Database Accession no. | | % Homology[a] |
|---|---|---|---|
| Substance P | P41333[SP] | RPKPQQFFGLM (SEQ ID NO: 5) | |
| Buforin II | BBU 736002.1[GB] | TRSSRAGLQFPVGRVHRLLRK (SEQ ID NO: 2) | |

The suffix [SP] signifies accession numbers in the Swiss Protein database.
The suffix [GB] signifies accession numbers in the GeneBank database.

These results indicate that there is potential for long Buforinins to form a similar supersecondary structure of a reverse turn with helix bundling. See Table 3. Therefore, we have defined a new class of peptides, "Previns" which may be used to construct compounds such as Buforinins which includes Buforin I (39 amino acids), Buforin II (21 amino acids), Peptide 36 and Peptide 24, and other analogous peptides having a QF bond, that competitively inhibit BttxB protease activity.

TABLE 3

Computer-Aided Secondary Structure Prediction[a]

| | |
|---|---|
| VAMP2$_{55-94}$ | ERDQKLSELDDRADALQAGASQFETSAAKLKRKYWWKNLK (SEQ ID NO: 16) |
| Gibrat[b] | HHHHHHHHHHHHHHHHHCCHHHHHHHHHHHHHHTTHHTCT |
| Nnpredict[c] | --------HH-HHHHHHH---HHHHHHHHHHHHHHH---- |
| B-I | AGRGKQGGKVRAKAKTRSSRAGLQFPVGRVHRLLRKGNY (SEQ ID NO: 17) |
| Gibrat | HTTTTTCCEEEEHHHHHHHHHCTEEEEHHHHEEEETTTC |
| Nnpredict | ---------EHE-----------E----HHHHHHH---- |
| B-I truncated 5 amino acids on both ends | QGGKVRAKAKTRSSRAGLQFPVGRVHRLL (SEQ ID NO: 11) |
| Gibrat | HCCHHEEHHHHHHHHHCCEEEECHEHEEE |
| Nnpredict | --------E----HHHHHH- |

[a]H, helix; E, sheet C, coil; T, turn; -, no prediction. QF cleavage site is indicated in bold.
[b]Garnier J. et al. (1987)J. Mol. Biol. 120: 97-120.
[c]McCleland D. G, Rumelhart D. E. In Explorations in Parallel Distributed Processing. 3: 318-362. 1988. MIT Press, Cambridge MA; Kneller D. G., et al. (1990)J. Mol. Biol. 214: 171-182.

These Previns or core structures are generally described by the formula:

$$B_1Z^*_2B_3Z^*_4X^*_5Q_6F_7X_8X_9X_{10}X_{11} \quad (1),$$

$$B_1X_2X_3X_4X_5Q_6F_7X_8X_9X_{10}X_{11} \quad (2), \text{ or}$$

$$B_1X_2B_3X_4Z_5Q_6F_7Z_8X_9X_{10}X_{11} \quad (3)$$

and the salts, esters, amides, and acyl forms thereof Each position represented by a letter indicates a single amino acid residue: B is a basic or polar/large amino acid or a modified form thereof; X is a small or hydrophobic amino acid or a modified form thereof; X* is a small or polar/large amino acid or a modified form thereof; Z is a polar/large or hydrophobic amino acid or a modified form thereof; Z* is Proline or a polar/large or hydrophobic amino acid or a modified form thereof. As described below, one or more of the peptide linkages between the amino acid residues may be replaced by a peptide linkage mimic.

The invention compounds include those core structures represented by formula (1), (2) and (3).

The amino terminus of the peptide may be in the free amino form or may be acylated by a group of the formula RCO—, wherein R represents a hydrocarbyl group of 1-6C. The hydrocarbyl group is saturated or unsaturated and is typically, for example, methyl, ethyl, i-propyl, t-butyl, n-pentyl, cyclohexyl, cyclohexene-2-yl, hexene-3-yl, hexyne-4-yl, and the like.

The C-terminus of the peptides of the invention may be in the form of the underivatized carboxyl group, either as the free acid or an acceptable salt, such as the potassium, sodium, calcium, magnesium, or other salt of an inorganic ion or of an organic ion such as caffeine. The carboxyl terminus may also be derivatized by formation of an ester with an alcohol of the formula ROH, or may be amidated by an amine of the formula $NH_3$, or $RNH_2$, or $R_2NH$, wherein each R is independently hydrocarbyl of 1-6C as defined above. Amidated forms of the peptides wherein the C-terminus has the formula $CONH_2$ are preferred.

The peptides of the invention may be supplied in the form of the acid addition salts. Typical acid addition salts include those of inorganic ions such as chloride, bromide, iodide, fluoride or the like, sulfate, nitrate, or phosphate, or may be salts of organic anions such as acetate, formate, benzoate and the like. The acceptability of each of such salts is dependent on the intended use, as is commonly understood.

The amino acids in the peptides of the invention may be those encoded by the gene or analogs thereof, and may also be the D-isomers thereof A preferred embodiment is a compound having the core structure of the formula (1), (2) or (3) wherein the compound is resistant to protease activity by having at least some of its residues in the D-configuration and retains the ability to inhibit BttxB protease activity.

The amino acid notations used herein are conventional and are as follows:

| Amino Acid | One-Letter Symbol | Three-Letter Symbol |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |

-continued

| Amino Acid | One-Letter Symbol | Three-Letter Symbol |
|---|---|---|
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

The compounds of the invention are peptides or peptide-like compounds which are partially defined in terms of amino acid residues of designated classes. Amino acid residues can be generally subclassified into major subclasses as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH.

Basic: The residue has a positive charge due to association with H ion at physiological pH or within one or two pH units thereof (e.g., histidine) and the residue is attracted by aqueous solution so as to seek the surface positions in the conformation of a peptide in which it is contained when the peptide is in aqueous medium at physiological pH.

Hydrophobic: The residues are not charged at physiological pH and the residue is repelled by aqueous solution so as to seek the inner positions in the conformation of a peptide in which it is contained when the peptide is in aqueous medium.

Neutral/polar: The residues are not charged at physiological pH, but the residue is not sufficiently repelled by aqueous solutions so that it would seek inner positions in the conformation of a peptide in which it is contained when the peptide is in aqueous medium. This description also characterizes certain amino acids as "small" since their side chains are not sufficiently large, even if polar groups are lacking, to confer hydrophobicity. "Small" amino acids are those with four carbons or less when at least one polar group is on the side chain and three carbons or less when not.

It is understood, of course, that in a statistical collection of individual residue molecules some molecules will be charged, and some not, and there will be an attraction for or repulsion from an aqueous medium to a greater or lesser extent. To fit the definition of "charged," a significant percentage (at least approximately 25%) of the individual molecules are charged at the relevant pH. The degree of attraction or repulsion required for classification as polar or nonpolar is arbitrary and, therefore, amino acids specifically contemplated by the invention have been classified as one or the other. Most amino acids not specifically named can be classified on the basis of known behavior.

Amino acid residues can be further subclassified as cyclic or noncyclic, and aromatic or nonaromatic, self-explanatory classifications with respect to the side-chain substituent groups of the residues, and as small or large. The residue is considered small if it contains a total of four carbon atoms or less, inclusive of the carboxyl carbon, provided an additional polar substituent is present; three or less if not. Small residues are, of course, always nonaromatic.

For the naturally occurring protein amino acids, subclassification according to the foregoing scheme is as follows.

| | |
|---|---|
| Acidic | Aspartic acid and Glutamic acid |
| Basic | Noncyclic: Arginine, Lysine |
| | Cyclic: Histidine |
| Small | Glycine, Serine, Alanine, Threonine, Cysteine |
| Polar/large | Asparagine, Glutamine |
| Hydrophobic | Tyrosine, Valine, Isoleucme, Leucine, |
| | Methionine, Phenylalanine, Tryptophan |

The gene-encoded secondary amino acid proline is a special case due to its known effects on the secondary conformation of peptide chains, i.e. helix structure disruptions. Therefore, proline may only be allowed in position 26 where it would help to disrupt the helix structures found on both sides of the QF cleavage site and force the helix-turn-helix structure.

Cysteine is a small amino acid. Generally, there are no cysteine or methionine in the sequences of the VAMP2 substrate, B-I, B-II, Peptide 24, Peptide 36. The side chain of cysteine is somewhat hydrophobic, but it is highly reactive. The sulfur moiety has the potential to react with the sulfur in other cysteine to from a cystine or disulfide bond. Cysteine may be modified so as to prevent its participation in the secondary structure. Additionally, cysteine may be used as a spacer anchor in a compound of formula (1), (2) or (3). Furthermore, it may be advantageous to incorporate cysteine for use as a reactive site to label a core structure with fluorescent markers.

The "modified" amino acids that may be included in the core structures are gene-encoded amino acids which have been processed after translation of the gene, e.g., by the addition of methyl groups or derivatization through covalent linkage to other substituents or oxidation or reduction or other covalent modification. The classification into which the resulting modified amino acid falls will be determined by the characteristics of the modified form. For example, if lysine were modified by acylating the, -amino group, the modified form would not be classed as basic but as polar/large amino acid.

Certain commonly encountered amino acids, which are not encoded by the genetic code, include, for example, beta-alanine (beta-Ala), or other omega-amino acids, such as 3-aminopropionic, 2,3-diaminopropionic (2,3-diaP), 4-aminobutyric and so forth, alphaaminisobutyric acid (Aib), sarcosine (Sar), ornithine (Orn), citrulline (Cit), t-butylalanine (t-BuA), t-butylglycine (t-BuG), N-methylisoleucine (N-McIle), phenylglycine (Phg), and cyclohexylalanine (Cha), norleucine (Nle), 2-naphthylalanine (2-Nal); 1,2,3,4-tetrahydroisoquinoline-3-carboxylic acid (Tic); 3-2-thienylalanine (Thi); methionine sulfoxide (MSO); and homoarginine (Har). These also fall conveniently into particular categories.

Based on the above definitions,

Sar, beta-Ala and Aib are small;

t-BuA, t-BuG, N-McIle, Nle, Mvl, Cha, Phg, Nal, Thi and Tic are hydrophobic;

2,3-diaP, Orn and Har are basic;

Cit, Acetyl Lys and MSO are neutral/polar/large.

The various omega-amino acids are classified according to size as small (beta-Ala and 3-aminopropionic) or as large and hydrophobic (all others).

Other amino acid substitutions, which are not gene encoded, are included in peptide compounds within the scope of the invention and can be classified within this general scheme according to their structure. For example, D-amino acid substitutions would be desirable to circumvent potential stability problems due to endogenous protease activity; especially important for an oral dosage route.

In all of the compounds of the invention, one or more amide linkages (—CO—NH—) may optionally be replaced with another linkage which is an isostere such as —CH$_2$NH—, —CH$_2$S—, —CH$_2$CH$_2$, —CH=CH— (cis and trans), —COCH$_2$—, —CH(OH)CH$_2$— and —CH$_2$SO—. This replacement can be made by methods known in the art. The following references describe preparation of peptide analogs which include these alterative-linking moieties: Spatola, A. F., *Vega Data* (March 1983), Vol. 1, Issue 3, "Peptide Backbone Modifications" (general review); Spatola, A. F., in "Chemistry and Biochemistry of Amino Acids Peptides and Proteins," B. Weinstein, eds., Marcel Dekker, New York, p. 267 (1983) (general review); Morley, J. S., *Trends Pharm Sci* (1980) pp. 463-468 (general review); Hudson, D., et al., *Int J Pept Prot Res* (1979) 14:177-185 (—CH$_2$NH—, —CH$_2$CH$_2$—); Spatola, A. F., et al., *Life Sci* (1986) 38:1243-1249 (—CH2—S); Hann, M. M., *J Chem Soc Perkin Trans I* (1982) 307-314 (—CH—CH—, cis and trans); Almquist, R. G., et al., *J Med Chem* (1980) 23:1392-1398 (—COCH$_2$—); Jennings-White, C., et al., *Tetrahedron Lett* (1982) 23:2533 (—COCH$_2$—); Szelke, M., et al., European Application EP 45665 (1982) CA: 97:39405 (1982) (—CH(OH)CH$_2$—); Holladay, M. W., et al., *Tetrahedron Lett* (1983) 24:4401-4404 (—C(OH) CH$_2$—); and Hruby, V. J., *Life Sci* (1982) 31:189-199 (—CH$_2$—S—).

Typical compounds within the scope of the invention are:

| | |
|---|---|
| RPKPQQFFGLM | (SEQ ID NO: 1) |
| TRSSRAGLQFPVGRVHRLLRK | (SEQ ID NO: 2) |
| TRAARAGLQFPVGRVHRLLRK | (SEQ ID NO: 3) |
| TRLLRAGLQFPVGRVHRLLRK | (SEQ ID NO: 4) |
| RAKPQQFFGLM | (SEQ ID NO: 5) |
| RAKAQQFFGLM | (SEQ ID NO: 6) |
| RAKAQQFPGLM | (SEQ ID NO: 7) |
| RAKLQQFPGLM | (SEQ ID NO: 8) |
| RAKGLQFPGLM | (SEQ ID NO: 9) |
| RAGLGQFFGLM | (SEQ ID NO: 10) |
| DAARAK*GLQFP*GLMAKLK | (SEQ ID NO: 11) |
| DAARAK*GLQPP*GLLAKLK | (SEQ ID NO: 12) |

```
                                     -continued
                                                            (SEQ ID NO: 13)
     TRSRAKGLQFPGLMVHRL (SEQ ID NO: 14)
                XQF----------------------Y
``` wherein "-" is a spacer molecule and "X" is any suitable amino acid sequence homologous to those upstream of the QF site of SEQ ID NOs: 1-12

"Active" compounds are defined as those compounds having the core sequence of the invention and inhibit BttxB and/or Tttx protease activities. The conformation of the compounds of the invention may be determined by circular dichroism. See CBnaves, J. M., et al. (1998) J. Biol. Chem. 273:43214-34221. Proton NMR may also be used. See Yi, G. et al. (1996) FEBS Lett. 398:87-90. X-ray crystallography may also be used. See Sutton, R. B., et aL (1998) Nature 395, 347-353.

"Derivatives" are defined as those compounds having a core sequence of the invention and contain amino acid modifications comprising 'unnatural' amino acids other than the known 21 amino acids (20 common, and then selenocysteine, which is an uncommon but naturally occurring non-gene encoded amino acid) or additions such as cysteine and lysine on termini to provide a reactive center for conjugation to other chemicals, labels or proteins.

Compounds of the formula (1), (2) or (3) may be used to construct compounds optimized for inhibiting the protease activity of BttxB or Tttx. Optimization may be done by substituting amino acids that promote helical structure formation upstream of the QF site. Examples of such are peptides having the amino acid sequences are shown in FIG. 7.

Substance P is a weak inhibitor of BttxB. It contains an alpha helical structure downstream of a QF site. It does not have an alpha helical structure upstream of the QF site. Computer modeling has been used to construct compounds which are similar to Substance P, yet contain alpha helices upstream and downstream of the QF site. Thus, compounds such as Substance P may be utilized as a molecular building block for constructing more potent BttxB inhibitors which potent inhibitors may comprise Buforinins. Therefore Substance P is considered a core structure within the scope of the compounds of the invention.

For example, Substance P may be modified by 4 substitutions, P2A, G3K, P4L, Q5G, to obtain a compound having the sequence, RAGLGQEFFGLM (SEQ ID NO: 10). These substitutions are predicted to generate the helical structures required for inhibition of BttxB protease activity. See Garcia et al. J. Applied Toxicology, in press.

In another embodiment, a spacer could be utilized in a Substance P like molecular building block in order to place a Tyrosine (~21 angstroms) from the F residue of the QF site as the location of Tyr is important since its removal in the B-I should a decrease in inhibition.

Suitable spacers include: Bis-Maleimidethane (BMOE) 8 Angstroms spacer arm; 1,4-Bis-maleimidobutane (BMB) 10.9 Angstoms spacer arm. See Chen, L. L. et al. J. Biol. Chem. 266:18237-18243, Yi, F. et al. J. Biol. Chem. 266: 3900-3906.

As shown below, there is an apparent similarity in the position of Tyr for B-I, VAMP2 and peptide 36:

```
AGRGKQGGKVRAKAKTRSSRAGLQFPVGRVHRLLRKGNY  (SEQ ID NO: 17)    Buforin I

ERDQKLSELDDRADALQAGASQFETSAAKLKRKYWWKNLK  (SEQ ID NO: 16)   VAMP2₅₄₋₉₄

AGRGKQGGKVRAKAKTRSSRAGLQFPVGRVHRLLRK  (SEQ ID NO: 19)       peptide36

RPKPQQFFGLM------YYY
```

The deletion of the C-terminal three amino acids results in a decrease of inhibition of BttxB by 50% as compared with B-I. See Garcia et al. (1999) J Applied Toxicol. in press. This indicates that the position of the Tyr residue may be important for the inhibitory function of the compounds.

Therefore a compound may be created from a Substance P like molecular building block to enhance its BttxB inhibitory ability by modifying the placement of Tyr or other hydrophobic amino acids an optimal distance from the QF cleavage site. This distance could be provided by peptide sequence or other suitable spacer molecules.

For example, a spacer incorporated upstream from the QF site in V2 sequence which would place Tyr around 6 angstroms from the Q of the QF site could improve inhibition. See Whitcome et al. (1996) FEBS Let. 386:133-136.

Spacers may be used to cross-link individual components to reach the desired distance. Such spacers include carbon chains of desired repetitions and length. A carbon chain spacer would be advantageous as it would confer resistance to cleavage and for esterification and amidation as well as neutralizing in the presence of base to form salts are all standard organic chemical techniques.

If the core structures of the invention are prepared under physiological conditions, the side-chain amino groups of the basic amino acids will be in the form of the relevant acid addition salts.

If the core structure is a peptide backbone comprised entirely of gene-encoded amino acids, or if some portion of it is so composed, the peptide or the relevant portion may also be synthesized using recombinant DNA techniques. The DNA encoding the core structures of the invention may be synthesized using standard techniques in the art such as solid phase DNA synthesis with conventional equipment that includes, for example, an ABI 3948 Nucleic Acid Synthesis System (Perkin Elmer Applied Biosystems, Foster City, Calif.) utilizing phosphoramidite synthesis chemistry (Beaucage, S. L. et al. (1981) Tetrahedron Lett. 22:1859-1862). DNA oligomers would be synthesized with overlapping matching complimentary sequences. Annealing of these sequences would form a double-stranded synthetic gene. Building on this process would give larger and larger double-stranded products till the requisite gene is built. Alternatively, DNA recombinant means would be employed by cloning the core structure of the invention, compounds containing the core structure, or like-fragment of H2A protein, and then modifying by site-directed mutagenesis or DNA-cassette replacement or other means in the art (Methods Enzymology vol. 152; Eds. S. L. Berge and A. R. Kimmel, Academic Press, Inc., Orlando, Fla., 1998) to achieve the modification desired. Codon choice can be integrated into the synthesis depending on the nature of the host.

For recombinant production, the DNA encoding the core structure is included in an expression system which places these coding sequences under the control of a suitable promoter and other control sequences which are compatible with an intended host cell. Types of host cells available span almost the entire range of the plant and animal kingdoms. Thus, the core structures of the invention or compounds containing the core structures could be produced in bacteria or yeast (to the extent that they can be produced in a nontoxic or refractile form or utilize resistant strains) as well as in animal cells, insect cells and plant cells.

The core structures of the invention or compounds containing the core structures can be produced in a form that will result in their secretion from the host cell by fusing to the DNA encoding the core structure of compound containing the core structure, a DNA encoding a suitable signal peptide, or may be produced intracellularly. They may also be degradation. Spacers and use of spacers are known in the art. See e.g., Synthetic Peptides Ed. G. A. Gant, W. H. Freeman & Co. New York, N.Y., 1992.

Alternatively, one may use amino acid residues to place the active moieties at appropriate distances from the QF site or create enhancing structures. For example, Cys may be used to manipulate a compound to have or not have a particular structure such as a disulfide loop. However, the use of other compounds such as TCEP, may adversely interact with such manipulated structures, i.e. the disulfide loop would be opened.

Consequently, one may use a Previn or a core structure of the formula (1), (2) or (3) to construct a Buforinin like compound or another compound which highly inhibits the protease activity of BttxB.

Preparation of the Invention Compounds

The invention compounds, often designated herein "Previns" are essentially core structures or molecular building blocks which may be modified at the N- or C-terminus and optimized for constructing compounds which inhibit the protease activity of BttxB or Tttx.

Standard methods can be used to synthesize core structures similar in size and conformation to the Previns. Most commonly used currently are solid phase synthesis techniques; indeed, automated equipment for systematically constructing peptide chains can be purchased. Solution phase synthesis can also be used but is considerably less convenient. When synthesized using these standard techniques, amino acids not encoded by the gene and D-enantiomers can be employed in the synthesis.

The N- and/or C-terminus can be modified with conventional chemical techniques. The compounds of the invention may optionally contain an acyl or an acetyl group at the amino terminus. Methods for acetylating or, more generally, acylating, the free amino group at the N-terminus are generally known in the art.

At the carboxy terminus, the carboxyl group may be present in the form of a salt; and in the case of pharmaceutical compositions, the salt will be a pharmaceutically acceptable salt. Suitable salts include those formed with inorganic ions such as $NH_4^+$, $Na^+$, $K^+$, $Mg^{++}$, $Ca^{++}$, and the like as well as salts formed with organic cations such as those of caffeine and other highly substituted amines. The carboxy terminus may also be esterified using alcohols of the formula ROH wherein R is hydrocarbyl (1-6C) as defined above. Similarly, the carboxy terminus may be amidated so as to have the formula —$CONH_2$, —CONHR, or —$CONR_2$, wherein each R is independently hydrocarbyl (1-6C) as herein defined. Techniques produced as fusion proteins with additional amino acid sequence which may or may not need to be subsequently removed prior to the use of these compounds as an inhibitor of BttxB protease activity.

Thus, the core structures of the invention can be produced in a variety of modalities including chemical synthesis and recombinant production or some combination of these techniques.

Any members of the Previn class which occur naturally are supplied in purified and isolated form. By "purified and isolated" is meant free from the environment in which the peptide normally occurs (in the case of such naturally occurring peptides) and in a form where it can be used practically. Thus, "purified and isolated" form means that the peptide is substantially pure, i.e., more than 90% pure, preferably more than 93% pure and more preferably more than 99% pure or is in a completely different context such as that of a pharmaceutical preparation.

The invention is also directed to the screening assays for compounds containing the core structures and assays utilizing the core structures and compounds containing the core structures.

The invention is also directed to the use of compounds containing the core structures as intracellular inhibitors of BttxB. Bttxs specifically target nerve cells because of the receptor-like recognition of cell surface gangliosides and synaptogamin by the nerve-cell targeting heavy chain (HC) subunit of the toxin. See Kozaki, S., et al. (1998) Microb. Pathog. 25:91-99. Once bound, the toxin is internalized by a mechanism not completely understood but apparently requires acidification of the endosome and cleavage of the disulfide bond linking the HC and the endoproteolytically active light chain (LC).

The specificity of this delivery system would be useful for delivery of compounds containing the core structures to those cell types poisoned or potentially poisoned with BttxB and could be used as a 'magic bullet' since the magic bullet approach is becoming a reality. See e.g. Pastan, L, et al. (1994) Ann. Rev. Biochem. 61:331-354 and Engert, A., et al. (1998) Curr. Top. Microbial. Immnunol. 234:13-33 (Introduction of immunotoxins linked to Diptheria toxin or Ricin A chain).

Therefore, the core structures or compounds containing the core structures may be linked to BttxB HC with a linkage such as a disulfide bond. Alternatively, the core structures or compounds containing the core structures may be linked to BttxB HC with a carrier protein such as human albumin or another bridge to form a multi-protein conjugate. This conjugate should then target the susceptible cells in a manner similar to BttxB. Once inside the cell, the conjugate may inhibit BttxB or the linkage may be cleaved to free the compound containing the core structure or carrier-core structure to inhibit BttxB protease activity.

Antibodies

Antibodies to the core structures may be produced using standard immunological techniques for production of polyclonal antisera and, if desired, immortalizing the antibody-producing cells of the immunized host for sources of monoclonal antibody production. Techniques for producing antibodies to any substance of interest are well known. It may be necessary to enhance the immunogenicity of the substance, particularly as here, where the material is only a short peptide, by coupling the hapten to a carrier. Suitable carriers for this purpose include substances which do not themselves produce an immune response in the mammal to be administered the hapten-carrier conjugate. Common carriers used include keyhole limpet hemocyanin (KLH), diphtheria toxoid, serum albumin, and the viral coat protein of rotavirus, VP6. Coupling of the hapten to the carrier is effected by standard techniques such as contacting the carrier with the peptide in the presence of a dehydrating agent such as dicyclohexylcarbodiimide or through the use of linkers such as those available through Pierce Chemical Company, Chicago, Ill.

The core structures or compounds containing the core structures in immunogenic form are then injected into a suitable mammalian host and antibody titers in the serum are monitored.

Polyclonal antisera may be harvested when titers are sufficiently high. Alternatively, antibody-producing cells of the host such as spleen cells or peripheral blood lymphocytes may be harvested and immortalized. The immortalized cells are then cloned as individual colonies and screened for the production of the desired monoclonal antibodies. The genes encoding monoclonal antibodies secreted by selected hybridomas or other cells may be recovered, manipulated if desired, for example, to provide multiple epitope specificity or to encode a single-chain form and may be engineered for expression in alternative host cells, such as CHO cells.

Thus, as used herein, "antibodies" also includes any immunologically reactive fragment of the immunoglobulins such as Fab, Fab' and F(ab')$_2$ fragments as well as modified immunoreactive forms such as Fv regions, which are produced by manipulation of the relevant genes (isolable, for example, from the appropriate hybridoma).

The antibodies of the invention are, of course, useful in immunoassays for determining the amount or presence of the core structures. Such assays are essential in quality controlled production of compositions containing the core structures of the invention. In addition, the antibodies can be used to assess the efficacy of recombinant production of the core structures, as well as for screening expression libraries for the presence of Previn encoding genes. They may also be used as affinity ligands for purifying and/or isolating the core structures and compounds containing the core structures. They may also be used for detecting and measuring core structures in sera or plasma by methods well known in the art such as RIA and ELISA. Therefore, one may monitor circulating Previns or compounds containing the core structures of the invention levels to assure sufficient dosage.

Compositions Containing the Previns and Methods of Use

The core structures are useful in constructing compounds that are effective in inhibiting the protease activity of bttxB and tetanus neurotoxins. Accordingly, compounds containing the core structures of the invention can be used in prevention, prophylaxis and therapies for BttxB and Tttx poisoning. For use in such contexts, a compound containing the core structure may be administered alone, or a variety of compounds containing the core structure and free Previns may be administered. Furthermore, additional protease inhibitors or adjunct chemicals such as tris-(2-carboxyethl) phosphine (TCEP) may be administered along with Previns or compounds containing the core structures of the invention.

TCEP is a non-odorous, non-sulfhydryl containing reducing agent that is relatively non-toxic in animals (P—$CH_2CH_2COOH)_3HCl$; Molecular Probes, Inc. Eugene, Oreg.). TCEP can reduce the disulfide bond between the HC and LC and allow the dissociation of the BttxB or Tttx subunits. This dissociation increases the availability of the active QF site to compounds which inhibit BttxB protease activity. Additionally, the disassociation of the toxin prevents nerve cell penetration. Other reducing agents such as dithiothreitol (DTT) may be used; however, they may be objectionable due to their distinctive odors and toxicity. Therefore, TCEP is preferred.

The core structures of the invention are also useful as standards in monitoring assays and in assays for evaluating the effectiveness of later-generation compounds containing the core structures. This could be done by utilizing the endopeptidase activity assay for BttxB. In this endopeptidase assay, one may evaluate whether potential peptides function as inhibitors or substrates of BttxB by the ability to cleave of a synthetic peptide substrate comprising amino acids 55-94 of the intracellular target VAMP2. The cleavage products may be separated by a $Cl_8$ reverse-phase HPLC column and detected by absorbance at 205 nm.

For preventing the initial intoxication or further poisoning caused by BttxB and Tttx in animal subjects, the core structures or compounds containing the core structures can be formulated as pharmaceutical or veterinary compositions. Depending on the subject to be treated, the mode of administration, and the type of treatment desired—e.g., prevention, prophylaxis, therapy; the core structures and the compounds containing the core structures are formulated in ways consonant with these parameters. A summary of such techniques is found in Remington's *Pharmaceutical Sciences*, latest edition, Mack Publishing Co., Easton, Pa.

In general, for use in treatment or prophylaxis, the Previns and compounds containing the core structure may be used alone or in combination with other compounds which inhibit protease activity such as VAMP2. Use of the enantiomeric forms containing all D-amino acids may confer advantages such as resistance to those proteases, such as trypsin and chymotrypsin.

The Previns and compounds containing the core structures can be administered singly or as mixtures of several Previns and compounds or in combination with other pharmaceutically active components, and in single or multiple administrations. The formulations may be prepared in a manner suitable for systemic administration. Systemic formulations include those designed for injection, e.g. intramuscular, intravenous or subcutaneous injection, or may be prepared for transdermal, transmucosal, or oral administration. The formulation will generally include a diluent as well as, in some cases, adjuvants, buffers, preservatives and the like. The Buforinins can be administered also in liposomal compositions or as microemulsions using conventional techniques.

If orally administered, the compounds of the invention must be protected from degradation in the stomach using a suitable enteric coating. This may be avoided to some extent by utilizing amino acids in the D-configuration, thus providing resistance to protease. However, the peptide is still susceptible to acid hydrolysis; thus, some degree of enteric coating may still be required.

The manner of administration and formulation of the compounds useful in the invention and their related compounds will depend on the nature of the condition, the severity of the condition, the particular subject to be treated, and the judgment of the practitioner; formulation will depend on mode of administration. As the compounds of the invention are small molecules, they are conveniently administered by oral administration by compounding them with suitable pharmaceutical excipients so as to provide tablets, capsules, syrups, and the like. Suitable formulations for oral administration may also include minor components such as buffers, flavoring agents and the like. Typically, the amount of active ingredient in the formulations will be in the range of 5%-95% of the total formulation, but wide variation is permitted depending on the carrier. Suitable carriers include sucrose, pectin, magnesium stearate, lactose, peanut oil, olive oil, water, and the like.

The compounds useful in the invention may also be administered through suppositories or other transmucosal vehicles. Typically, such formulations will include excipients that facilitate the passage of the compound through the mucosa such as pharmaceutically acceptable detergents.

The compounds may also be administered topically, for topical conditions such as psoriasis, or in formulation intended to penetrate the skin. These include lotions, creams, ointment and the like which can be formulated by known methods.

The compounds may also be administered by injection, including intravenous, intramuscular, subcutaneous or intraperitoneal injection. Typical formulations for such use are liquid formulations in isotonic vehicles such as Hank's solution or Ringer's solution.

Suitable alternative formulations also include nasal sprays, liposomal formulations, slow-release formulations, and the like.

Any suitable formulation may be used. A compendium of art-known formulations is found in *Remington's Pharmaceutical Sciences*, latest edition, Mack Publishing Company, Easton, Pa. Reference to this manual is routine in the art.

A preferred means to deliver the Previns and compounds containing the core structures of the invention would include the use TCEP. Since TCEP cleaves the holotoxin which yields a site available to the active moieties of the core structures. TCEP also disassociates the toxins into individual components which prevents nerve cell penetration. Also, the core structures could be coupled to a variety of compounds including a BttxB heavy chain, which excludes the toxin light chain, to target the Previn or the compound containing the core structure to the toxin affected cells.

The dosages of the compounds of the invention will depend on a number of factors which will vary from patient to patient.

The following examples are intended to illustrate but not to limit the invention.

EXAMPLE 1

Endopeptidase Activity Assay

The toxin was activated immediately prior to use by incubating at 25° C. for 30 minutes in an activation mixture that contained, in a volume of 7.5 µl per digest: 2.4 µg (16 pmol) of toxin, 30 mM NaHEPES buffer, pH 7.3, and 5 mM DTT or TCEP. A substrate peptide mix was prepared that contained 1 nmol of the substrate peptide (VAMP2 55-94), 4% DMSO, 4% Triton X-100, and 80 mM NaHEPES buffer, pH 7.3, per digest. The final reaction mix was made by adding 25 µl of the substrate peptide mix, 4.5 µl of fresh 10 mM DTT, 13 µl $H_2O$ or test peptide, and 7.5 µl of activation mixture. The reaction was initiated by incubation at 37° C. The reaction was stopped by the addition of 1 vol trifluoroacetic acid (TFA) to 0.25%. The samples were clarified by centrifugation.

In this assay, 16 pmol of BttxB digested 1 nmol of the substrate to completion in less than 45 min. at 37° C.

EXAMPLE 2

Reverse Phase HPLC Analysis of Digestion Products

Digested peptide products were fractionated by RP-HPLC on a Waters: Bondapak analytical $C_{18}$ column (3.9 mm×30 cm) attached to Beckman 126 pumps and a model 168 Diode Array Detector, controlled by Beckman System Gold Ver 8.1 software. The solvent system consisted of buffer A (BA; $H_2O$-0.1% TFA) and buffer B (BB; $CH_3CN$-0.1% TFA). The development program consisted of the following: 97% BA, 0-1 min; to 33% BB, 1-30 min; then wash with 97% BB for 5 min, followed by equilibration in 97% BA for 10 min. The flow rate was ml $min^{-1}$ except during the wash and equilibrium phase where it was 1.5 ml $min^{-1}$. 75 µl injections were made with a Waters Intelligent Sample Processor (WISP Model 712). The effluent was monitored at dual wavelengths of 205 and 280 nm.

Initially, digestion products are identified by peptide sequencing using automated Edman-degradation on an ABI 477A protein sequencer attached in-line with a HPLC (ABI model 120A) for detection of phenlythiohydratoin derivatized amino acids. The extent of digestion was determined by comparison of peak areas of undigested controls (no added toxin) and total digests (digests allowed to go to completion, typically 2-3 h). The extent of inhibition or digestion will be determined from examination of the chromatograms by peak area comparison with standards and/or products formed compared with quantified standards or digests without added inhibitor that have gone to completion.

EXAMPLE 3

Secondary Structure Predictions

Secondary structures were predicted by using the nnpredict, and the Gibrat (GOR2) programs. See McCleland, D. G, Rumelhart D. E. In Explorations in Parallel Distributed Processing. vol. 3:318-362. 1988. MIT Press, Cambridge, Mass.; Kneller D. G., et al. (1990) J. Mol. Biol. 214:171-182; Garnier, J. et al. (1978) J. Mol. Biol 198;425-443; Garnier J. et al. (1987) J. Mol. Biol. 120:97-120; Garnier, J., et al. (1996) Methods Enzymol. 266:540-553. Helical wheel projections were made using the Antheprot program Ver 4. See Deleage, G., Instit de Biologie et Chimi des Protéins, Lyon, France.

The Gibrat program predicts that B-I could form an alpha-helical-turn-alpha-helical configuration similar to that of VAMP2. See Table 3. The result that Buforin I may form a secondary structure similar to VAMP2 then suggests that B-I may also form a similar supersecondary structure of a reverse turn with helix bundling similar to VAMP2. See Lebeda, et. al. (1996). In support of this prediction, we found that the diminishing inhibition of BttxB activity and its helical content as Buforin-I was truncated, mirrors the diminishing activity of BttxB for substrate deletions. See data for Buforin-II in Table 1 and FIG. 4.

EXAMPLE 4

Preparation of Buforinins, Previns and Compounds Containing the Core Structures

The Buforinins and compounds containing the core structures may be obtained from amphibian stomach by gut lavage using methods as described by Park, C. B. et al. See Park, C. B., et al. (1996) Biochem. Biophys. Res. Comm. 218: 408-413.

The Buforinins and compounds containing the core structures may be synthesized by solid-phase peptide synthesis (SSPS) as described by L. A. Carpino, J. Am. Chem. Soc. 79,4427 (1957), C. D. Chang et al., Int. J. Pept. Protein Res. 11,246 (1978), E. Atherton, et al., J. Chem Soc. Chem. Commun., 537 (1978) and R. B. Merrifield, J. Am. Chem. Soc. 85, 2149 (1963) and Barlos, K., et al., (1989) Tetrahedron Lett. 30:3947.

The Buforinins, Previns and compounds containing the core structures may also be produced by DNA recombinant means commonly known in the art whereby a suitable promoter for expression in heterologous systems, i.e. bacterial, fungi, insect, or mammalian cell cultures may be used. The DNA sequence may be optimized for the particular host and tRNA content. For example, a compound such as a Buforinin or other which contains the core sequence of the invention may be enzymatically digested to isolate the core sequence.

Once isolated, recombinant means may be used to modify the core sequence or add additional amino acids or other moieties onto the core sequence in order to make a compound that effectively inhibits the protease activity of BttxB or Tttx.

EXAMPLE 5

Inhibition of Protease Activity by Buforinins

The endopeptidase assay and reverse phase HPLC as described in Examples 1 and 2 may be used to detect the cleavage products and the extent of protease inhibition. Briefly, potential inhibitors may be added to the substrate peptide mix immediately before the addition of the activation mix containing the toxin as described in Garica, et al. After incubation for 45 min at 37° C., the reaction should be stopped and the digestion products may be analyzed by using RP HPLC. If a fluorescent-labeled substrate is used then product formation will be determined with an in-line fluorescent detector.

The extent of inhibition or digestion will be determined as described in Example 2 of undigested substrate remaining and/or products formed compared with quantified standards or digests without added inhibitor that have gone to completion.

Alternative means can be used include densitometry wherein the substrates and products separated by electrophoresis and stained with protein specific dyes, i.e. Coomassie brilliant blue, and measured. One may also perform immunoassays to determine the extent of inhibition or digestion by utilizing substrate or product specific antibodies.

Alternatives also include in vivo protection or tissue-specific function assays. For example, an experimental animal would be dosed with the inhibitor with or with out adjuncts and then challenged with the toxin, e.g. i.v. injection of a Buforinin with a reducing agent such as TCEP. The onset of symptoms or an alteration of the $LD_{50}$ would then be evaluated. Tissue protection assays would employ an intact nerve-muscle-preparation wherein muscle twitch response to nerve cell stimulation would be evaluated. The toxin would be preincubated with a Buforinin and adjuncts and are then added to the tissue preparation.

EXAMPLE 6

Figure 6B:
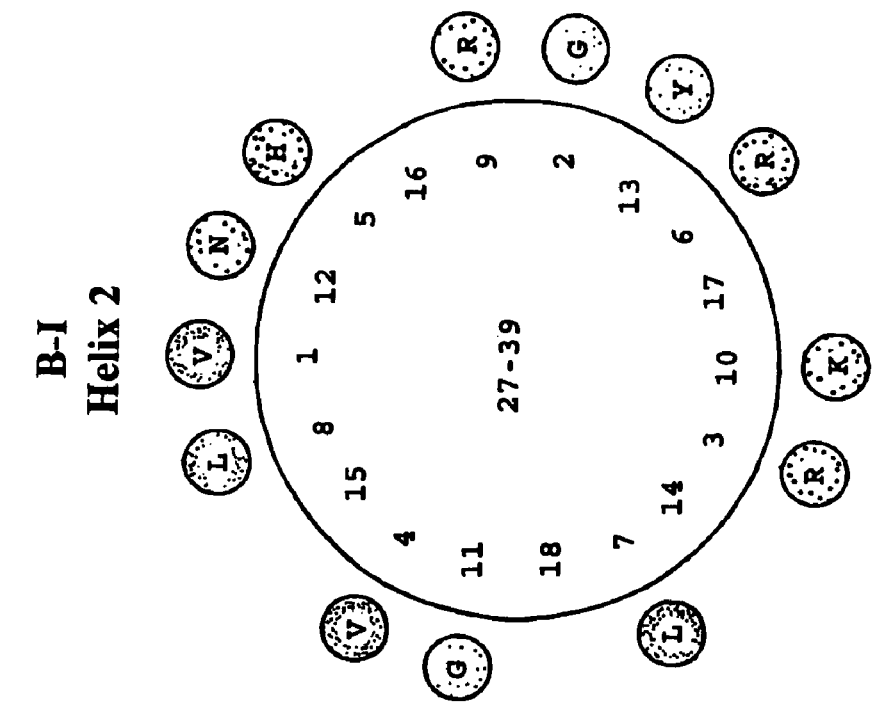
FIG. 6 shows (A) a comparison of the amino acid sequences of Buforin I (SEQ ID NO: 17), and Mutant B-I R11L (SEQ ID NO: 25) and mutant B-I R11L, K15L, S18L (SEQ ID NO: 15); (B) a helical wheel projections for Buforin I of Helix I and Helix 2; and (C) a helical wheel projections fro Helix 1 of mutants B-I R11L and B-I R11L, K15L, S18L.
Figure 6B:
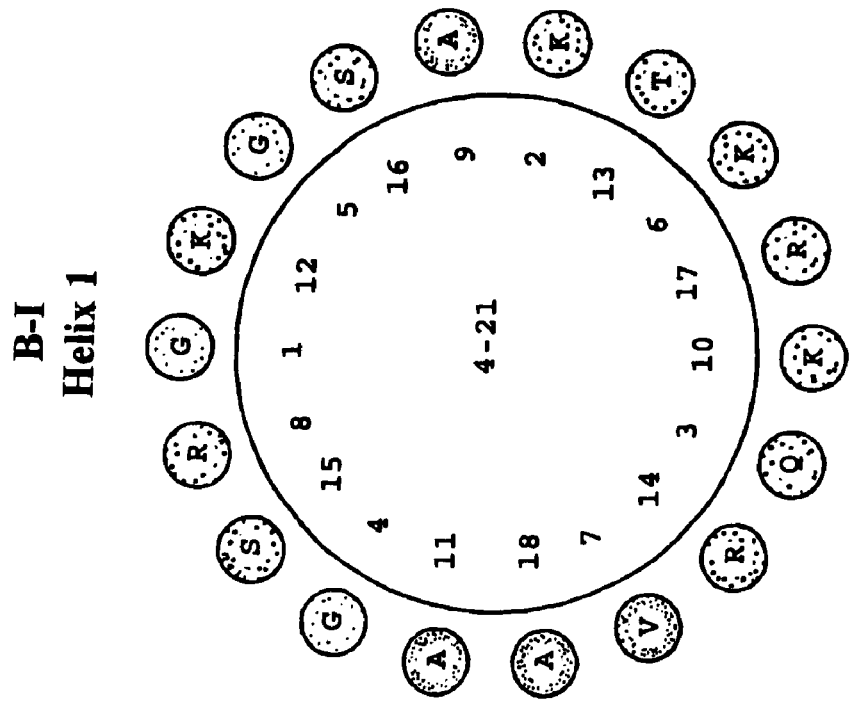
Figure 6C:
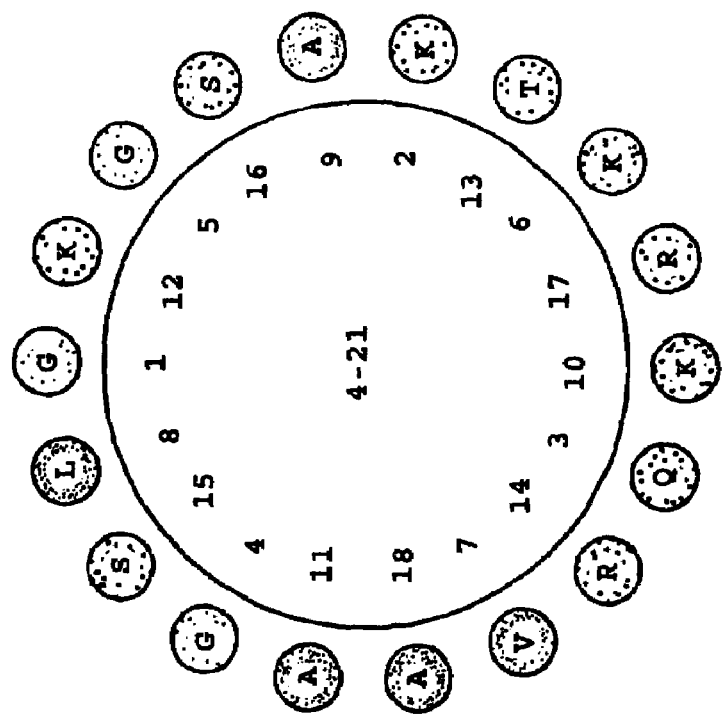
Figure 6C:
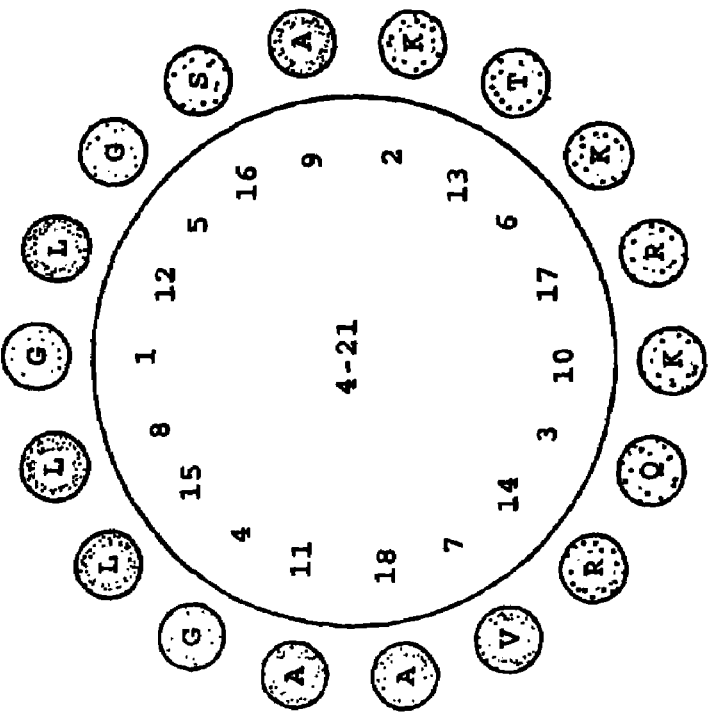

Designing Buforinins, Previns and Other Compounds having the Core Sequences of the Invention with an Effect on BttxB Protease Activity By using standard methods and techniques, the peptides of the invention may be modified by either making mutations or substitutions which include substituting $Pro_{26}$ with glutamine to make the active site more like the substrate, or other amino acid, that favors turn formation without the turn constraint imposed by Pro. Such substitutions are predicted to result in more effective helix bundling for toxin association to occur. Other amino acid substitutions or mutations in the helix region could be made so that either the helix becomes more amphipathic to improve helix bundling or improve interaction with the toxin. Such changes would include a substitution of R11 with L or another helix favoring amino acid. See FIGS. 6A and B. Similarly, multiple substitutions R11, K15L, and S18L or other amino acids could be made to favor helix formation and bundling.

Alternatively, B-II which lacks the predicted upstream helix of B-I may be modified to enhance and improve its ability to inhibit BttxB protease activity. For example, a peptide having substitutions S3A and S4A (SEQ ID NO:5) has a predicted helix upstream of the QF site. Another example would be a peptide having substitutions S2L and S4L (SEQ ID NO:6). Likewise, this peptide has a predicted helix upstream of the QF site.

EXAMPLE 7

Pretreatment with Buforinins, Previns and Other Compounds having a Core Sequence of the Invention Buforinins, Previns, and other compounds having the core sequence of the invention may be used to pretreat food and liquids that might be contaminated with BttxB or Tttx. For example, an effective amount of a Buforinin, Previn, or other compound having the core sequence may be mixed into water having BttxB to inhibit the protease activity of the BttxB, e.g. 100 ml of water containing 1 ug of BttxB would be treated with 100 ug of a Buforinin, Previn, or other compound and 0.1 mmol reducing agent, i.e. TCEP in tablet, powder, or liquid form.

These various forms would comprise of a Buforinin, Previn, or other compound having the core structure, reducing agent such as TCEP, and other fillers and stabilizers. A liquid form could be made from a tablet or powder that is pre-dissolved prior to use. A solution having a Buforinin, Previn, or other compound containing a core structure of the invention may be applied on the surface of solid food having BttxB on the surface. Alternatively, an effective amount of the solution may be used to treat solid food which has been ground into small particles in order to allow the active ingredient of the solution access to amounts of BttxB which is not found on the surface of the food.

Contaminated or suspect non-food surfaces may also be washed with solutions of containing a Buforinin, Previn, or other compound having the core structure of the invention. The compounds of the invention could be applied as a spray, foam, towelette, or sponge used to soak or wipe the surface. The amounts would be typically 200 ug per ml of solution applied; however, the concentrations required would depend on the extent of contamination and the appropriate concentration of the active ingredients may be adjusted as needed.

EXAMPLE 8

Prophylaxis Uses

Buforinins, Previns, and other compounds having the core sequence of the invention could be used as a prophylactic against BttxB or Tttx poisoning. Subjects could be treated with Buforinins, Previns, and other compounds having the core sequence of the invention prior to entering situations where they are likely to be in contact with BttxB or Tttx. The dosage mode and amount could be dependent on the amount of toxin expected to contact and the time in which contact might occur. The preferred administration for immediate contact would be i.v. The preferred form administration for a slower and more prolonged exposure would be by ingestion. However, other slow release forms of delivery such as a patch may be used.

EXAMPLE 9

Prevention of Aerosol Contamination

Buforinins, Previns, and other compounds having the core sequence of the invention may be incorporated into a disposable, moist-filter, breathing mask for inactivating BttxB in aerosol form. The toxin would be trapped in moist-filter whereupon it would inactivated by a Buforinin.

Such a filter design would protect against toxin particles smaller than bacteria, e.g. 1 micron such as HEPA. The filters could be supplied premoistened and impregnated with Buforinins, Previns, or other compounds having the core sequence of the invention and adjunct chemicals such as TCEP. Alternatively, the filters could be prepared by wetting a dry filter pre-impregnated or by soaking the filter in a solution of Buforinins, Previns, or other compounds having the core sequence of the invention. Enclosed areas that have air processing capabilities may also be protected in this fashion with appropriate sized filters.

EXAMPLE 10

Wound Treatment

Open lesions could be treated with topical applications having Buforinins, Previns, or other compounds having the core sequence of the invention to inhibit BttxB or Tttx poisoning before the toxin has a chance to be absorbed into the body. A powder mixture containing Buforinins and adjuncts which include a reducing agent and other stabilizers or fillers may be applied directly to the wound. This approach relies on the wound weeping to dissolve the Buforinins, Previns, or other compounds having the core sequence of the invention. Alternatively, an ointment, liquid, spray, foam, or towelette having Buforinins, Previns, or other compounds having the core sequence of the invention may be applied to the wound surface. The towelette could be supplied or made in a similar manner as the filters of Example 10.

EXAMPLE 11

Post Exposure

Subjects already suffering from BttxB or Tttx poisoning could be treated with Buforinins, Previns, or other compounds having the core sequence of the invention. These of treatments would scavenge accessible toxin not yet compartmentalized into susceptible cells. Intoxication of susceptible cells leads to cell function inhibition but is not itself lethal to the cells. Given sufficient time the cells can recover and become functional again. This recovery process may last up to several months. Therefore, treatment with Buforinins, Previns, or other compounds having the core sequence of the invention will aid in the recovery of the subject and reduce the need of alternative life supporting measures. The treatment may comprise use of Buforinin-BttxB HC or other Previns or other compounds having the core sequence of the invention like conjugates. The Bttx-HC portion would specifically direct the conjugate to susceptible cells where uptake would occur in a manner similar as the toxin. Inside the cell, the conjugates would access to the toxin and inhibit the proteast activity, thereby protecting the cell against further toxin damage until the toxin is removed from the cells by endogenous proteolysis.

EXAMPLE 12

Identification of a Botulinum Toxin Subclass

Boforinins, Previns, or other compounds having the core sequence of the invention may be used for the identification of BttxB or Tttx. An unknown Bttx or Tttx would be incubated with substrates and a Buforinin, Previn, or other compound having the core sequence of the invention that would specifically inhibit BttxB and Tttx if present. Detection of uncleaved substrate or reduction of digest products would allow the identification of the toxin.

This may be useful as a confirming assay since the inhibition is specific. For example, a C-terminal fluorescent-labeled substrate, such as VAMP2, would be attached to microtiter plates. See Hallis, B., et al. (1996) J. Clin. Microbiol. 34:1934-1938. The unknown sample is then added to the well and allowed to incubate. The reaction would be stopped and the well rinsed. Reduction of fluorescence would indicate susceptibility of the substrate to the toxin. If Buforinins, Previns, or other compounds having the core sequence of the invention are included in the digest mix then BttxB or Tttx toxin would be specifically inhibited and the fluroescence levels would be higher than those reactions containing BttxB without inhibitor.

EXAMPLE 13

Construction of Compounds having Core Structures Optimized for Inhibiting the Protease Activity of Botulinum B toxin Core structures of the formula (1), (2) or (3) may be optimized by making modifications or substitutions in the sequence such as those shown in FIG. 7. These core structures may then be used to construct compounds which highly inhibit the protease activity of Botulinum B toxin.

For example, by using standard methods and techniques, the core structures of the invention may be modified by either making mutations or substitutions and amino acid additions which favor turn formation. Other amino acid additions, mutations or substitutions could be made so that either the helix becomes more amphipathic to improve helix bundling or improve interaction with the toxin.

Incorporation by Reference

To the extent necessary to understand or complete the disclosure of the present invention, all publications, patents, and patent applications mentioned herein are expressly incorporated by reference therein to the same extent as though each were individually so incorporated.

The invention claimed is:

1. A pharmaceutical composition for treating Botulinum or tetanus intoxication which comprises a protease inhibitory amount of a peptide or salts, esters, amides and acyl forms thereof, wherein the peptide is selected from the group consisting of

| | |
|---|---|
| TRAARAGLQFPVGRVHRLLRK, | (SEQ ID NO: 3) |
| TRLLRAGLQFPVGRVHRLLRK, | (SEQ ID No: 4) |
| RAKAQQFFGLM, | (SEQ ID NO: 6) |
| RAKAQQFPGLM, | (SEQ ID NO: 7) |
| RAKLQQFPGLM, | (SEQ ID NO: 8) |
| RAKGLQFPGLM, | (SEQ ID NO: 9) |
| RAGLGQFFGLM, | (SEQ ID NO: 10) |
| DAARAKGLQFPGLMAKLK, | (SEQ ID NO: 11) |
| DAARAKGLQFPGLLAKLK, and | (SEQ ID NO: 12) |
| TRSRAKGLQFPGLMVHRL | (SEQ ID NO: 13). |

2. The pharmaceutical composition of claim 1, wherein the salt is a phosphate.

3. The pharmaceutical composition claim 2, wherein the phosphate salt is formed by phosphorylation of serine, threonine and or tyrosine.

4. The pharmaceutical composition of claim 1 further comprising tris-(2-carboxyethyl)phosphine (ICEP).

5. The pharmaceutical composition of claim 4 further comprising biocompatable chaotropes.

6. The pharmaceutical composition of claim 5, wherein the biocompatible chaotropes is hydroxyurea or 2-oxo-1 pyridine acetamide.

7. A peptide in purified and isolated form, or salts, esters, amides and acyl forms thereof selected from the group consisting of

| | |
|---|---|
| TRAARAGLQFPVGRVHRLLRK, | (SEQ ID NO: 3) |
| TRLLRAGLQFPVGRVHRLLRK, | (SEQ ID NO: 4) |
| RAKAQQFFGLM, | (SEQ ID NO: 6) |
| RAKAQQFPGLM, | (SEQ ID NO: 7) |
| RAKLQQFPGLM, | (SEQ ID NO: 8) |
| RAKGLQFPGLM, | (SEQ ID NO: 9) |
| RAGLGQFFGLM, | (SEQ ID NO: 10) |
| DAARAKGLQFPGLMAKLK, | (SEQ ID NO: 11) |
| DAARAKGLQFPGLLAKLK, | (SEQ ID NO: 12) |
| TRSRAKGLQFPGLMVHRL | (SEQ ID NO: 13). |

8. A kit for treating Botulinum toxin B or Tetanus toxin intoxication comprising at least one peptide of claim 7.

9. The peptide of claim 7, wherein the salt is a phosphate.

10. The peptide of claim 9, wherein the phosphate salt is formed by phosphorylation of serine, threonine and or tyrosine.

* * * * *

SEQUENCE LISTING

<160> NUMBER OF SEQ ID NOS: 26

<210> SEQ ID NO 1
<211> LENGTH: 11
<212> TYPE: PRT
<213> ORGANISM: Homo sapiens

<400> SEQUENCE: 1

Arg Pro Lys Pro Gln Gln Phe Phe Gly Leu Met
 1               5                  10

<210> SEQ ID NO 2
<211> LENGTH: 21
<212> TYPE: PRT
<213> ORGANISM: Bufo gargarizans

<400> SEQUENCE: 2

Thr Arg Ser Ser Arg Ala Gly Leu Gln Phe Pro Val Gly Arg Val His
 1               5                  10                  15

Arg Leu Leu Arg Lys
            20

<210> SEQ ID NO 3
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Thr Arg Ala Ala Arg Ala Gly Leu Gln Phe Pro Val Gly Arg Val His
 1               5                  10                  15

Arg Leu Leu Arg Lys
            20

<210> SEQ ID NO 4
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Thr Arg Leu Leu Arg Ala Gly Leu Gln Phe Pro Val Gly Arg Val His
 1               5                  10                  15

Arg Leu Leu Arg Lys
            20

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Ala Lys Pro Gln Gln Phe Phe Gly Leu Met
 1               5                  10

<210> SEQ ID NO 6

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Ala Lys Ala Gln Gln Phe Phe Gly Leu Met
  1               5                   10

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Ala Lys Ala Gln Gln Phe Pro Gly Leu Met
  1               5                   10

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Ala Lys Leu Gln Gln Phe Pro Gly Leu Met
  1               5                   10

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Ala Lys Gly Leu Gln Phe Pro Gly Leu Met
  1               5                   10

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Ala Gly Leu Gly Gln Phe Phe Gly Leu Met
  1               5                   10

<210> SEQ ID NO 11
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11
```

-continued

Asp Ala Ala Arg Ala Lys Gly Leu Gln Phe Pro Gly Leu Met Ala Lys
1               5                   10                  15

Leu Lys

<210> SEQ ID NO 12
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asp Ala Ala Arg Ala Lys Gly Leu Gln Phe Pro Gly Leu Leu Ala Lys
1               5                   10                  15

Leu Lys

<210> SEQ ID NO 13
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Thr Arg Ser Arg Ala Lys Gly Leu Gln Phe Pro Gly Leu Met Val His
1               5                   10                  15

Arg Leu

<210> SEQ ID NO 14
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Any suitable amino acid
<220> FEATURE:
<221> NAME/KEY: MOD_RES
<222> LOCATION: (3)..(18)
<223> OTHER INFORMATION: Any suitable amino acid

<400> SEQUENCE: 14

Xaa Gln Phe Xaa Xaa Xaa Xaa Xaa Xaa Xaa Xaa Xaa Xaa Xaa Xaa Xaa
1               5                   10                  15

Xaa Xaa Tyr

<210> SEQ ID NO 15
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Thr Arg Ser Arg Ala Lys Gly Leu Gln Phe Pro Gly Leu Leu Val His
1               5                   10                  15

Arg Leu Leu Arg Lys Gly Asn Tyr
                20

<210> SEQ ID NO 16
<211> LENGTH: 40
<212> TYPE: PRT
<213> ORGANISM: Homo sapiens

<400> SEQUENCE: 16

Glu Arg Asp Gln Lys Leu Ser Glu Leu Asp Asp Arg Ala Asp Ala Leu
1               5                   10                  15

Gln Ala Gly Ala Ser Gln Phe Glu Thr Ser Ala Ala Lys Leu Lys Arg
            20                  25                  30

Lys Tyr Trp Trp Lys Asn Leu Lys
        35                  40

<210> SEQ ID NO 17
<211> LENGTH: 39
<212> TYPE: PRT
<213> ORGANISM: Bufo gargarizans

<400> SEQUENCE: 17

Ala Gly Arg Gly Lys Gln Gly Gly Lys Val Arg Ala Lys Ala Lys Thr
1               5                   10                  15

Arg Ser Ser Arg Ala Gly Leu Gln Phe Pro Val Gly Arg Val His Arg
            20                  25                  30

Leu Leu Arg Lys Gly Asn Tyr
        35

<210> SEQ ID NO 18
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Thr Arg Ser Ser Arg Ala Gly Leu Gln Phe Pro Val Gly Arg Val His
1               5                   10                  15

Arg Leu Leu Arg Lys Gly Asn Tyr
            20

<210> SEQ ID NO 19
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ala Gly Arg Gly Lys Gln Gly Gly Lys Val Arg Ala Lys Ala Lys Thr
1               5                   10                  15

Arg Ser Ser Arg Ala Gly Leu Gln Phe Pro Val Gly Arg Val His Arg
            20                  25                  30

Leu Leu Arg Lys
        35

<210> SEQ ID NO 20
<211> LENGTH: 38
<212> TYPE: PRT
<213> ORGANISM: Bufo gargarizans

<400> SEQUENCE: 20

Gly Arg Gly Lys Gln Gly Gly Lys Val Arg Ala Lys Ala Lys Thr Arg

```
                1               5                  10                 15
Ser Ser Arg Ala Gly Leu Gln Phe Pro Val Gly Arg Val His Arg Leu
            20                  25                 30

Leu Arg Lys Gly Asn Tyr
        35

<210> SEQ ID NO 21
<211> LENGTH: 38
<212> TYPE: PRT
<213> ORGANISM: Gallus gallus

<400> SEQUENCE: 21

Gly Arg Gly Lys Gln Gly Gly Lys Ala Arg Ala Lys Ala Lys Ser Arg
  1               5                  10                 15

Ser Ser Arg Ala Gly Leu Gln Phe Pro Val Gly Arg Val His Arg Leu
            20                  25                 30

Leu Arg Lys Gly Asn Tyr
        35

<210> SEQ ID NO 22
<211> LENGTH: 29
<212> TYPE: PRT
<213> ORGANISM: Bufo gargarizans

<400> SEQUENCE: 22

Gln Gly Gly Lys Val Arg Ala Lys Ala Lys Thr Arg Ser Ser Arg Ala
  1               5                  10                 15

Gly Leu Gln Phe Pro Val Gly Arg Val His Arg Leu Leu
            20                  25

<210> SEQ ID NO 23
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(17)
<223> OTHER INFORMATION: Any suitable amino acid

<400> SEQUENCE: 23

Arg Pro Lys Pro Gln Gln Phe Phe Gly Leu Met Xaa Xaa Xaa Xaa Xaa
  1               5                  10                 15

Xaa Tyr Tyr Tyr
            20

<210> SEQ ID NO 24
<211> LENGTH: 10
<212> TYPE: PRT
<213> ORGANISM: Unknown Organism
<220> FEATURE:
<223> OTHER INFORMATION: Description of Unknown Organism: Illustrative
      peptide

<400> SEQUENCE: 24

Glu Leu Asp Asp Arg Ala Asp Ala Leu Gln
  1               5                  10

<210> SEQ ID NO 25
<211> LENGTH: 39
<212> TYPE: PRT
<213> ORGANISM: Bufo gargarizans
```

```
<400> SEQUENCE: 25

Ala Gly Arg Gly Lys Gln Gly Gly Lys Val Leu Ala Lys Ala Lys Thr
 1               5                  10                  15

Arg Ser Ser Arg Ala Gly Leu Gln Phe Pro Val Gly Arg Val His Arg
            20                  25                  30

Leu Leu Arg Lys Gly Asn Tyr
        35

<210> SEQ ID NO 26
<211> LENGTH: 39
<212> TYPE: PRT
<213> ORGANISM: Bufo gargarizans

<400> SEQUENCE: 26

Ala Gly Arg Gly Lys Gln Gly Gly Lys Val Leu Ala Lys Ala Leu Thr
 1               5                  10                  15

Arg Leu Ser Arg Ala Gly Leu Gln Phe Pro Val Gly Arg Val His Arg
            20                  25                  30

Leu Leu Arg Lys Gly Asn Tyr
        35
```